United States Patent
Li et al.

(10) Patent No.: US 9,514,412 B2
(45) Date of Patent: Dec. 6, 2016

(54) TECHNIQUES FOR DETECTING DECEPTIVE ANSWERS TO USER QUESTIONS BASED ON USER PREFERENCE RELATIONSHIPS

(71) Applicant: Google Inc., Mountain View, CA (US)

(72) Inventors: Fangtao Li, Mountain View, CA (US); Shuchang Zhou, Beijing (CN)

(73) Assignee: Google Inc., Mountain View, CA (US)

( * ) Notice: Subject to any disclaimer, the term of this patent is extended or adjusted under 35 U.S.C. 154(b) by 328 days.

(21) Appl. No.: 14/100,523

(22) Filed: Dec. 9, 2013

(65) Prior Publication Data
US 2015/0161513 A1    Jun. 11, 2015

(51) Int. Cl.
*G06N 5/04*    (2006.01)
*G06K 9/62*    (2006.01)
*A61B 5/16*    (2006.01)

(52) U.S. Cl.
CPC .............. *G06N 5/04* (2013.01); *A61B 5/164* (2013.01); *G06K 9/62* (2013.01)

(58) Field of Classification Search
None
See application file for complete search history.

(56) References Cited

PUBLICATIONS

Guha et al. (Guha04), Propagation of trust and distrust. In WWW '04: Proceedings of the 13th international conference on World Wide Web, pp. 403-412 [online], 2004 [retrieved on Nov. 2, 2015]. Retrieved from the Internet:<URL:http://www.google.com/url?sa=t &rct=j&q=&esrc=s&source=web&cd=1 &ved=0CB4QFjAAahUKEwjOj8Hs-fHlAhWG5yYKHaCJCKl &url>.*
Li, F. et al., "Deceptive Answer Prediction with User Preference Graph," Proceedings of the 51st Annual Meeting of the Association for Computational Linguistics, pp. 1723-1732, Sofia, Bulgaria, Aug. 4-9, 2013.

\* cited by examiner

*Primary Examiner* — Stanley K Hill
*Assistant Examiner* — Nathan Brown, Jr.
(74) *Attorney, Agent, or Firm* — Remarck Law Group PLC

(57) ABSTRACT

A computer-implemented method can include receiving, at a computing device having one or more processors, questions and answers, each question having one or more answers, and each question and each answer being associated with a particular user. The method can include receiving, at the computing device, evaluations of the answers from users. The method can include identifying, at the computing device, at least one of textual and contextual features for each answer to obtain sets of features. The method can include generating, at the computing device, a user preference graph indicating relationships between users associated with at least one of the questions, the answers, and the evaluations. The method can also include detecting, at the computing device, whether each specific answer is a deceptive answer based on its set of features and the user preference graph.

20 Claims, 4 Drawing Sheets

TECHNIQUES FOR DETECTING DECEPTIVE ANSWERS TO USER QUESTIONS BASED ON USER PREFERENCE RELATIONSHIPS

FIELD

The present disclosure relates to community question/answer websites and, more particularly, to techniques for detecting deceptive answers to user questions based on user preference relationships.

BACKGROUND

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

Question and answer (QA) websites can provide a service where a user can input a question and other users can provide answers to the question. Users of QA websites can also provide feedback with respect to the various answers to the question. This feedback can include a "best answer" based on voting/selections and/or whether a particular answer is "helpful." Because these QA websites are often publicly accessible, a person can pose unhelpful, inaccurate, or otherwise inappropriate answers. These answers can be deceptive and thus can be referred to as deceptive answers. For example, an answer from such a person can be deceptive because it fulfills an agenda, such as advertising, as opposed to an authentic answer. Deceptive answers can also be problematic when mining question/answer pairs to train models or to help provide a best answer in response to a question at a computing device.

SUMMARY

A computer-implemented method is presented. The method can include receiving, at a computing device having one or more processors, questions and answers, each question having one or more answers, and each question and each answer being associated with a particular user. The method can include receiving, at the computing device, evaluations of the answers from users. The method can include identifying, at the computing device, at least one of textual and contextual features for each answer to obtain sets of features. The method can include generating, at the computing device, a user preference graph indicating relationships between users associated with at least one of the questions, the answers, and the evaluations. The method can also include determining, at the computing device, a measure of deceptiveness for each answer based on its set of features and the user preference graph.

In other embodiments, the method further includes detecting, at the computing device, whether a specific answer is a deceptive answer by comparing its measure of deceptiveness to a threshold indicative of deceptive answers.

In some embodiments, the method further includes determining, at the computing device, one or more additional features for each answer based on the user preference graph by regularizing the user preference graph and using a linear weight model.

In other embodiments, detecting whether each specific answer is deceptive includes detecting whether each specific answer is a deceptive answer based on its set of features and its one or more additional features.

In some embodiments, the evaluations indicate at least one of (i) a best answer for a specific question, (ii) an indication that a specific answer is helpful, and (iii) an indication that the specific answer is not helpful.

In other embodiments, the textual features for a specific question include at least one of: (i) a unigram, (ii) a bigram, (iii) a universal resource locator (URL), (iv) a phone number, (v) an electronic mail (e-mail) address, and (vi) a length of the specific answer, wherein specific unigrams and bigrams corresponding to an intent to promote are indicative of deceptive answers, wherein URLs, phone numbers, and e-mail addresses are indicative of deceptive answers, and wherein lengthy answers are indicative of deceptive answers.

In some embodiments, the contextual features for a specific answer include a relevance to its corresponding question, and wherein a lack of relevance of the specific answer to its corresponding question is indicative of a deceptive answer.

In other embodiments, the method further includes determining, at the computing device, the relevance of the specific answer to its corresponding question by utilizing at least one of: (i) a vector space model, (ii) a translation model, and (iii) a topic model.

In some embodiments, the contextual features for a specific answer include at least one of: (i) past user activity statistics, (ii) a user authority score, (iii) robot-indicative features, (iv) evaluation from other users, and (v) duplication with other users.

In other embodiments, the questions, the answers, and the associated users are retrieved from a question/answer website.

In some embodiments, the method further includes: filtering, at the computing device, the answers to obtain filtered answers by removing the deceptive answers from the answers, and outputting, from the computing device, the filtered answers.

A computing device is also presented. The computing device can include a communication device and one or more processors. The communication device can be configured to receive questions and answers, each question having one or more answers, and each question and each answer being associated with a particular user. The communication device can also be configured to receive evaluations of the answers from users. The one or more processors can be configured to identify at least one of textual and contextual features for each answer to obtain sets of features. The one or more processors can be configured to generate a user preference graph indicating relationships between users associated with at least one of the questions, the answers, and the evaluations. The one or more processors can also be configured to determine a measure of deceptiveness for each answer based on its set of features and the user preference graph.

In other embodiments, the one or more processors are further configured to detect whether a specific answer is a deceptive answer by comparing its measure of deceptiveness to a threshold indicative of deceptive answers.

In some embodiments, the one or more processors are further configured to determine one or more additional features for each answer based on the user preference graph by regularizing the user preference graph and using a linear weight model.

In other embodiments, the one or more processors are configured to detect whether each specific answer is a deceptive answer based on its set of features and its one or more additional features.

In some embodiments, the evaluations indicate at least one of (i) a best answer for a specific question, (ii) an indication that a specific answer is helpful, and (iii) an indication that the specific answer is not helpful.

In other embodiments, the textual features for a specific question include at least one of: (i) a unigram, (ii) a bigram, (iii) a universal resource locator (URL), (iv) a phone number, (v) an electronic mail (e-mail) address, and (vi) a length of the specific answer, wherein specific unigrams and bigrams corresponding to an intent to promote are indicative of deceptive answers, wherein URLs, phone numbers, and e-mail addresses are indicative of deceptive answers, and wherein lengthy answers are indicative of deceptive answers.

In some embodiments, the contextual features for a specific answer include a relevance to its corresponding question, and wherein a lack of relevance of the specific answer to its corresponding question is indicative of a deceptive answer.

In other embodiments, the one or more processors are further configured to determine the relevance of the specific answer to its corresponding question by utilizing at least one of: (i) a vector space model, (ii) a translation model, and (iii) a topic model.

In some embodiments, the contextual features for a specific answer include at least one of: (i) past user activity statistics, (ii) a user authority score, (iii) robot-indicative features, (iv) evaluation from other users, and (v) duplication with other users.

In other embodiments, the questions, the answers, and the associated users are retrieved from a question/answer website.

In some embodiments, the one or more processors are further configured to filter the answers to obtain filtered answers by removing the deceptive answers from the answers, and the communication device is further configured to output the filtered answers.

Further areas of applicability of the present disclosure will become apparent from the detailed description provided hereinafter. It should be understood that the detailed description and specific examples are intended for purposes of illustration only and are not intended to limit the scope of the disclosure.

BRIEF DESCRIPTION OF THE DRAWINGS

The present disclosure will become more fully understood from the detailed description and the accompanying drawings, wherein.

DETAILED DESCRIPTION

By filtering out deceptive answers, question and answer (QA) websites can provide more accurate answers to users, which can result in an improved user experience. Further, models can be better trained using filtered answers to questions that are mined from QA websites. Deceptive answers can be detected based on answer quality, e.g., a semantic quality of the answer. High quality answers, however, can be deceptive answers. For example, a spammer can provide a high quality answer that is well-written, informative, and responsive to the question, but is still a deceptive answer, such as by advertising a specific service. Similarly, low quality answers may not be deceptive answers. For example, non-native speakers of a particular language may provide an authentic answer that is determined to be low quality due to misspellings and/or grammar mistakes and is thus labeled as a deceptive answer.

Accordingly, techniques for detecting deceptive answers to user questions based on user preference relationships are presented. "Detecting" deceptive answers can involve predicting that answers are deceptive before any or much user (community) feedback is provided, which can allow for these deceptive answers to be filtered and removed before contaminating a QA website. Alternatively, the deceptive answers can be detected and filtered out, such as when mining question-answer pairs from a QA website to train model(s) or determine a best answer for a user question. The term "malicious user" as used herein can refer to a spammer that utilizes deceptive answers to promote a target product/service or any other user that provides deceptive answers to questions.

The techniques can identify at least one of (i) textual features and (ii) contextual features of each answer. The techniques can also generate a user preference graph based on evaluations by the users. The users may represent a community of users of the QA website. These evaluations can indicate a preference of the users with respect to a particular answer, e.g., positive or negative. For example, positive evaluations can include "helpful" or "best answer," and negative answers can include "not helpful." The user preference graph can connect users having the same preferences to answers, e.g., a preference to authentic answers or deceptive answers. The user preference graph can be used to augment the deceptive answer prediction/detection based on the identified features.

Figure 1:
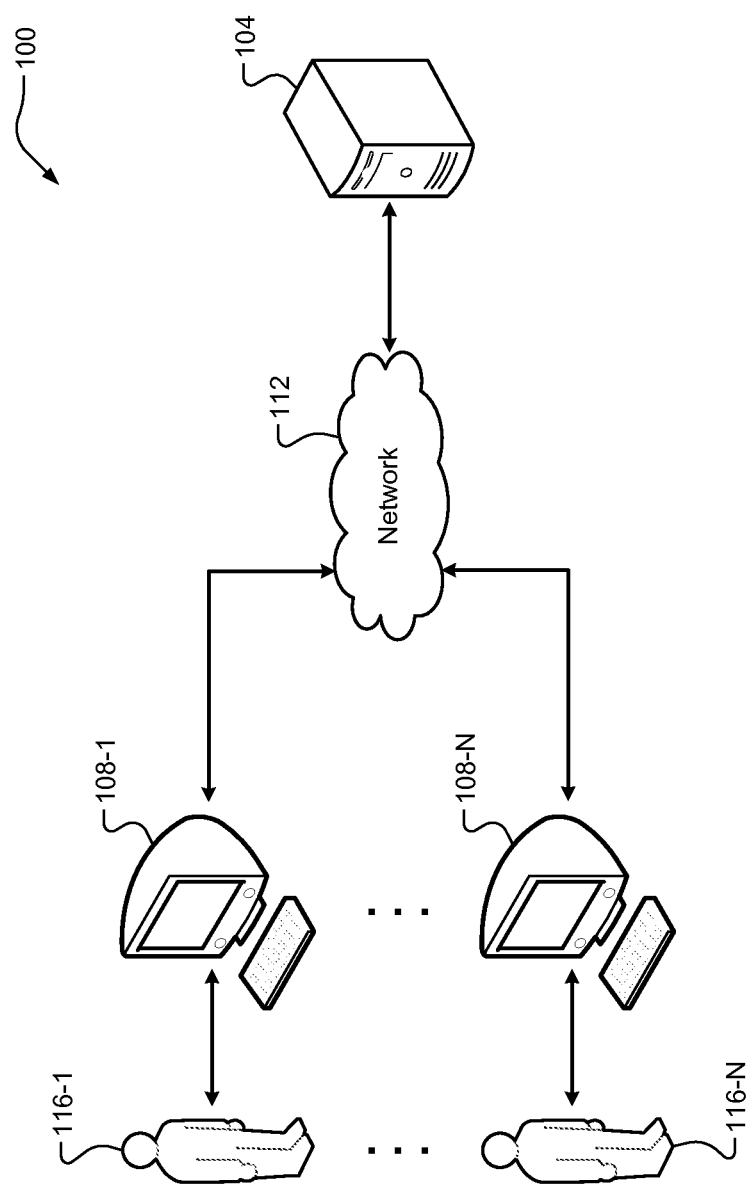
FIG. 1 is an example functional block diagram of a computing network according to some implementations of the present disclosure.

Referring now to FIG. 1, an example diagram of a computing network 100 is illustrated. The computing network 100 can include a server 104 configured to implement at least a portion of the techniques of the present disclosure. The term "server" as used herein can refer to any suitable computing device configured to execute the techniques of the present disclosure, as well as both a single server and two or more servers operating in a parallel or distributed architecture. The server 104 can be configured to communicate with a plurality of computing devices 108-1 ... 108-N (N≥1, collectively "computing devices 108") via a network 112. The network 112 can include a local area network (LAN), a wide area network (WAN), e.g., the Internet, or a combination thereof.

The computing devices 108 can be any suitable computing devices (desktop computers, laptop computers, tablet computers, mobile phones, etc.) configured to interact with users 116-1 ... 116-N (N≥1, collectively "users 116"), and communicate via the computing network 112, e.g., with the server 104. In one implementation, the users 116 can collectively represent a community of users at a QA website.

The QA website can be hosted at the server 104 or at another server on the network 112. While the server 104 is described as performing the techniques of the present disclosure, it should be appreciated that the one or more computing devices 108 can also be configured to partially or wholly perform the techniques of the present disclosure.

Figure 2:
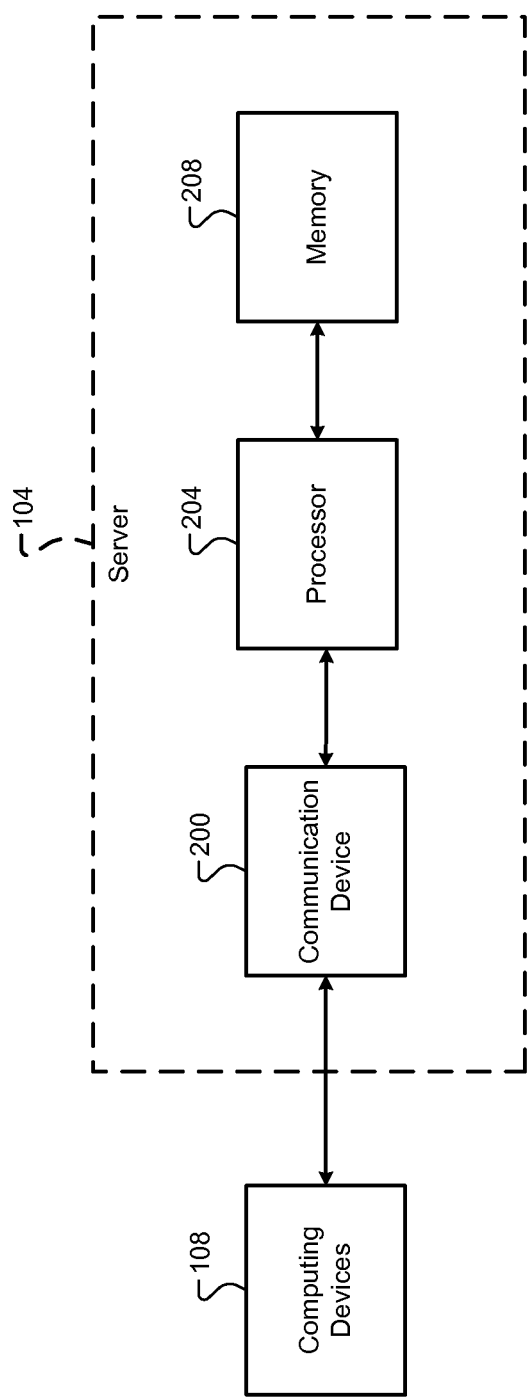
FIG. 2 is an example functional block diagram of a computing device of FIG. 1.

Referring now to FIG. 2, an example functional block diagram of the server 104 is illustrated. The server 104 can include a communication device 200, a processor 204, and a memory 208. The term "processor" as used herein can refer to both a single processor and two or more processors operating in a parallel or distributed architecture. The communication device 200 can include any suitable components, e.g., a transceiver, configured for communication via the network 112, e.g., with the computing device 104. The memory 208 can be any suitable storage medium (flash, hard disk, etc.) configured to store information at the server 104. The processor 204 can execute a set of instructions to perform the techniques of the present disclosure, which are described in greater detail below. For example, the set of instructions may be stored at the memory 208.

The processor 204 can receive answers to question(s) via the communication device 200. This information can also be referred to as question-answer pairs, where each question is associated with one or more answers. The questions and their answers can be obtained directly from users and/or retrieved from a QA website. For example, the questions and answers can be mined from multiple QA websites and deceptive answers can be identified and filtered out to obtain filtered answers for training a model or providing a better answer to a user question. Alternatively, for example, the answers to a question can be received via the communication device 200 and deceptive answers can be predicted and filtered out by the processor 204 before being posted publicly at a QA website.

The processor 204 can identify features of each of the answers to a particular question. Identifying features of the answers can also be referred to as extracting features from the answers. Deceptive answer prediction can be viewed as a binary-classification problem. The processor 204 can identify two different kinds of features for an answer: (i) textual features of the answer and (ii) contextual features of the answer. Textual features can represent features of the content of the answers. For example, and as further described below, textual features can refer to features of the actual text of the answer (words, links, numbers, punctuation, etc.). Contextual features, on the other hand, represent features from the context of the answers. For example, and as further described below, contextual features can refer to features not of the actual text of the answer but related to the answer in another manner (user activity, user expertise, answer topic, etc.). In one implementation, identification of the textual and/or contextual features can involve a supervised learning process or a supervised learning framework. The processor 204 can also determine a user preference graph, which can be used in addition to the textual and contextual features to enhance the deceptive answer prediction/detection of the present disclosure.

The textual features can include unigrams and/or bigrams. A unigram can be a single word and a bigram can be two words. This textual feature can also be referred to as a bag-of-words. Certain unigrams/bigrams can be associated with deceptive answers, and thus answers containing these unigrams/bigrams can be more likely to be deceptive answers. In one implementation, an effective feature selection method can be utilized to select a top first number, e.g., 200, of unigrams and bigrams as features, and a top second number, e.g., 10, of these can be associated with deceptive answers. For example, a top 200 unigrams and bigrams can be selected, and a top 10 unigrams relating to an intent for promotion can be associated with deceptive answers. These top 10 unigrams relating to the intent for promotion can include "professional," "service," "advice," "address," "site," "telephone," "therapy," "recommend," "hospital," and "expert."

The textual features can also include universal resource locator (URL) features. Malicious users may promote their products/services by linking to a particular URL, and thus the presence of a URL in an answer can be indicative of a deceptive answer. Not all URLs, however, are necessarily indicative of deceptive answers. For example, a question asking about the weather in a particular place can have an answer of http://www.weather.com, which is an authentic answer. Thus, the textual features can further include a length of the URL and a popularity score of the URL. A longer (more specific) URL can be indicative of a deceptive answer, and a URL having a low popularity score can also be indicative of a deceptive answer.

The textual features can also include telephone numbers and/or electronic mail (e-mail) addresses. The presence of phone numbers or e-mails in an answer can be indicative of a deceptive answer. The textual features can also include answer length. The length of an answer can include at least one of (i) a number of characters in the answer, (ii) a number of words in the answer, and (iii) a number of sentences in the answer. A longer answer can be indicative of a deceptive answer, because these answers typically include additional promotional or otherwise malicious text as compared to a short/brief authentic answer.

The contextual features for an answer can include a relevance of the answer to the question. In other words, the question itself can be used as a contextual feature. The relevance of the answers to the question can be determined using one or more relevance models. An example relevance model is a vector space model. According to the vector space model, each answer or question can be viewed as a word vector. Given a question q and an answer a, the vector space model can use all weighted word counts, e.g., TF-IDF, as well as a cosine similarity (q·a) of their words vectors as relevant functions. The vector space model, however, may only consider exact word matches, and thus answers that are actually the same, e.g., "Barack Obama" and "President of the United States," can be determined to be different. To remedy word mismatch problems, relevance models at higher semantic levels can be used.

An example relevance model at a higher semantic level than the vector space model is a translation model. The translation model can be a mathematical model in which the language translation is modeled in a statistical way. The probability of translating a source sentence (the answer) into a target sentence (the question) can be obtained by aligning the words to maximize the product of all the word probabilities. The translation model can be trained using data mined from a QA website (community data), with a language of a question as the target language, and a language of its corresponding best answer as the source language. Using the translation model, translation scores can be computed for a new question and its answers. By using the translation model, answers by non-native speakers of the language of the question can be determined to be authentic and not incorrectly filtered out as deceptive.

Another example relevance model at a higher semantic level than the vector space model is a topic model. To reduce false negatives of word mismatch in the vector space model, the topic model can be used to extend matching to a semantic topic level by identifying topics of both the question and each answer in order to determine whether a particular answer is off-topic and thus a deceptive answer. One example topic model is a Latent Dirichlet Allocation (LDA) model, which considers a collection of documents with K latent topics, where K is much smaller than the number of words. The LDA model can map information from the word dimension to a semantic topic dimension in order to address the mismatch shortcomings of the vector space model.

The contextual features can also include user profile features. These features can be related to a user's profile for a particular QA website, and these features can indicate the user's past activity statistics (posted questions, posted answers, best answer/total answer ratio, etc.). Past activity statistics indicating frequent positive involvement at the QA website can be indicative of a user that provides authentic answers, whereas no past activity statistics or past activity statistics indicating infrequent and/or negative involvement at the QA website can be indicative of a user that provides deceptive answers.

The contextual features can also include a user authority score. The user authority score can represent an expertise score of a user. This can be related to an expert finding task. To compute an authority score for a user, a directed user graph can be constructed with the user interactions at the QA website (the community). The nodes of the user graph can represent users and an edge between two nodes can indicate a contribution from one user to another user. Specifically, at a QA website, an edge from node A to node B can be established when user B answers a question asked by user A, which can indicate that user B is more likely to be an authority or expert than user A. The weight of an edge can indicate the number of interactions between users.

The authority score (AS) for a user can be calculated based on a link analysis algorithm. The authority score can be computed iteratively with random initial values. One example of the link analysis algorithm is:

$$AS(u_i) = \frac{1-d}{N} + d \sum_{u_j \in M(u_i)} \frac{AS(u_j)}{L(u_j)}, \qquad (1)$$

where $u_1, \ldots u_n$ represents users of a collection of N total users, $u_j$ represents a user of a set of users $M(u_i)$ whose answers are provided by user $u_i$, $L(u_j)$ represents a number of users who answer questions by user $u_j$, and d is a damping factor. For example only, the damping factor d may be 0.85.

The contextual features can also include robot-indicative features. Robot indicative features can represent features that indicate that the answering user is machine (computer) implemented. The term "robot" can refer to a script created by a malicious user that is configured to automatically post answers. Distributions of answer-posting time can be noticeably different between human users and robot users. For example, some robot users may make posts continuously and mechanically, and thus the time increment between posts for robot users may be smaller than human users who need more time to think and process between posts. Based on this difference, a time sequence feature can be designed for robot user detection. For each author, a list of time points to post answers can be obtained.

This list of time points can be represented as $T=\{t_0, t_1, \ldots, t_n\}$, where $t_i$ is a time point when an $i^{th}$ answer is posted in response to a question. The time sequence T can be converted into a time interval sequence. The time interval sequence can be referred to as $\Delta T = \{\Delta t_0, \Delta t_1, \ldots, \Delta t_{n-1}\}$, where $\Delta t_i = t_{i+1} - t_i$. Based on the interval sequences for all users, a matrix can then be constructed having rows corresponding to users and columns corresponding to an interval histogram with a predefined range. The matrix can be represented as $X_{m \times b}$, where m represents the rows and b represents the columns. Each row vector can then be used as a time sequence pattern for robot user detection. To reduce noise and sparseness, a dimension reduction technique can be utilized to extract latent semantic features with Singular Valve Decomposition (SVD).

The contextual features can also include evaluation from other users. More particularly, other users can express their evaluation or opinions with respect to a particular answer. For example, the asker of the question can choose one of the provided answers as a "best answer." A Boolean feature can be used to denote if this answer is selected as the "best answer." In addition, other users can label each answer as "helpful" or "not helpful." This helpfulness evaluation by other users can also be used, and can be defined as a ratio between the number of "helpful" votes and the total number of votes.

The contextual features can also include duplication with other answers. Malicious users may repeatedly post the same pre-written promotion as an answer. Alternatively, they may post the same pre-written promotion and merely change the name of the product/service. Therefore, the similarity between answers can be computed. If two answers are identical or substantially identical, e.g., only the product/service name is changed, and the question is different, the answer can be detected as potentially deceptive. This similarity does not measure the semantic similarity between answers, but merely the similarity at a word level. Thus, a Bleu Score algorithm can be applied, which is a known metric in machine translation for measuring the overlap between n-grams of two text fragments. The duplication score of each answer can be the maximum Bleu Score compared to all other answers.

As previously discussed, the processor 204 can also determine a user preference graph that can augment the textual/contextual features to enhance the deceptive answer prediction/detection techniques of the present disclosure. This can be based on an assumption that users tend to perform similar behaviors (posting authentic answers vs. posting deceptive answers).

Figure 3C:
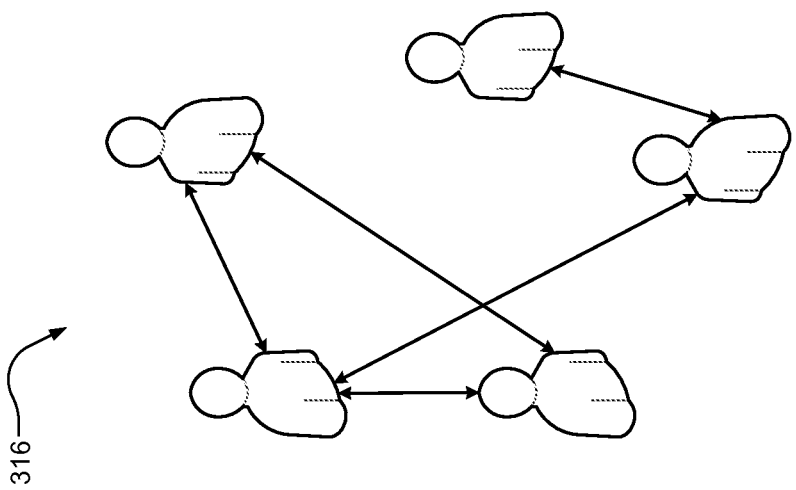
FIGS. 3A-3C are example diagrams of user interaction at a question and answer (QA) website, preference relationships amongst the users, and a user preference graph, respectively.
Figure 3B:
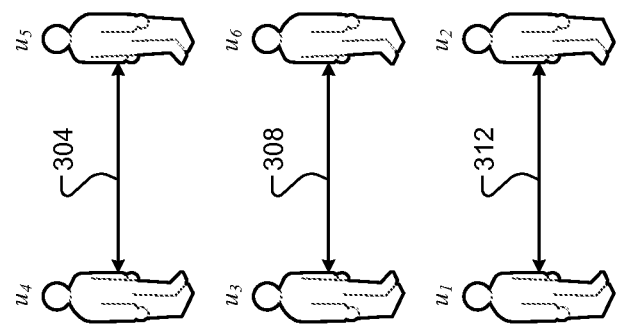
Figure 3A:
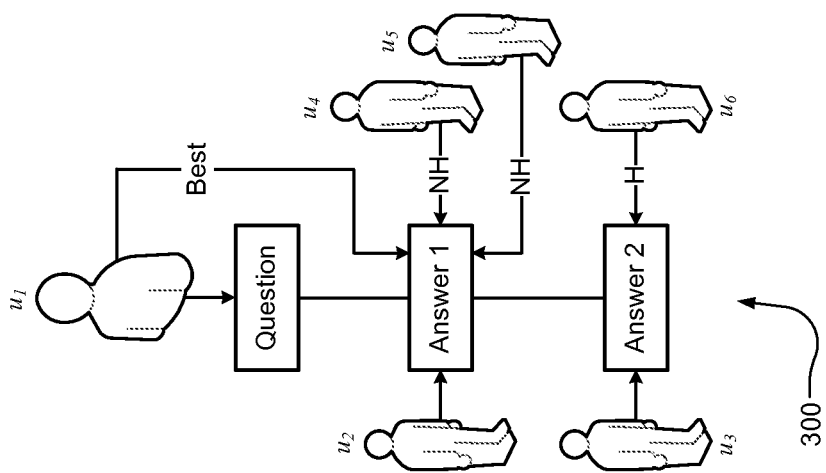

FIGS. 3A-3C illustrate an example question-answering process, example user preference relationships, and an example user preference graph, respectively. Specifically, FIG. 3A illustrates a general process in a question-answer thread 300. An asker $u_1$ asks a question. Then, there are answers to the question provided by users $u_2$ and $u_3$. After the answers are provided, users can vote each answer as "helpful" or "not helpful" to show their evaluation towards the answer. In this example, users $u_4$ and $u_5$ vote the first answer as "not helpful" ("NH") and user $u_6$ votes the second answer as "helpful" ("H"). The asker $u_1$ can also select the "best answer" ("Best") from among all the answers. In this example, the asker $u_1$ selects the first answer as the "best answer."

The relationship among users can focus on asker/answerer relationships, where it is assumed that the answerer is more knowledgeable than the asker. In the techniques of the present disclosure, however, it does not matter who is more knowledgeable. Instead, the techniques of the present disclosure aim to determine whether two users are authentic users or malicious users. Thus, the preference here is based on the answer evaluation. More specifically, if two users share the same preference towards a specific answer, they have a user preference relationship. The information used for evaluation these user preference relationships can include "helpful" or "not helpful" feedback. In this example, user $u_4$ and $u_5$ both gave a "not helpful" evaluation towards the first answer, and thus these users have a user preference relationship 304 as indicated in FIG. 3B.

Further, it can be assumed that the author of an answer gives a "helpful" evaluation of their answer. Thus, in this example, because user $u_6$ gave a "helpful" evaluation to the second answer, users $u_6$ and $u_3$ (the author) can have a user preference relationship 308 as indicated in FIG. 3B. The user preference can also be extracted using the "best answer" evaluation. More specifically, if the asker selects the "best answer," the asker can have a user preference relationship with the author of that answer. In this example, the asker $u_1$ can have a user preference relationship 312 with user $u_2$ as indicated in FIG. 3B. After extracting all user preference relationships in a set of questions and answers, e.g., a QA website (community), a complete user preference graph can be constructed. For example only, an example user preference graph 316 is shown in FIG. 3C, which includes nodes representing users and edges connecting users having user preference relationships, where edge weights are based on quantities of user preference relationships.

Malicious users can promote their objectives, e.g., target products/services, by promoting related deceptive answers. For example, a plurality of malicious users may collaboratively make deceptive answers seem authentic by providing positive evaluations ("helpful" or "best answer") to the deceptive answers. Authentic users, however, generally have their own judgments as to positive/negative answers, and thus the evaluation of an answer can reflect the relationship amongst users. In other words, authentic users can share the same evaluation of a specific answer, e.g., negative ("not helpful") and malicious users can share the same evaluation of the specific answer, e.g., positive. While these relationships can be noisy, e.g., due to authentic users mistakenly (being tricked into) providing positive feedback for a deceptive answer, the user preference graph can be used to generally improve accuracy of deceptive answer prediction/detection, which is now described in greater detail.

The user preference graph can be utilized to compute a feature value, which can then be added into the supervised method previously discussed herein as an additional feature to the textual/contextual features. A graph regularizer can be utilized to constrain the supervised parameter learning. This can be based on a linear weight model $f(\cdot)$ where a function value is determined by a linear combination of input features. In one implementation, the function can be defined as follows:

$$f(x_i) = w^T \cdot x_i = \sum_k w_k \cdot x_{ik}, \quad (2)$$

where $x_i$ is a K dimension feature vector for an $i^{th}$ answer, and a parameter value $w_k$ captures an effect of a $k^{th}$ feature in predicting a deceptive answer.

Best parameters (w*) can be found by minimizing an objective function. In one implementation, the objective function can be defined as follows:

$$\Omega_1(w) = \sum_i L(w^T x_i, y_i) + \alpha \cdot |w|_F^2, \quad (3)$$

where $L(w^T x_i, y_i)$ is a loss function that measures discrepancy between a predicted label $w^T \cdot x_i$ and a true label $y_i$, where $y_i \in \{1,-1\}$. Commonly used loss functions can include $L(p,y)=(p-y)^2$ (least square) and $L(p,y)=\ln(1+\exp(-py))$ (logistic regression). For simplicity, the least square loss function can be utilized. The term $|w|_F^2 = \Sigma_k w_k^2$ can represent a regularization term defined in terms of a Frobenius norm of the parameter vector w, and can be utilized to penalize overly complex models in order to avoid fitting.

The user preference graph can then be incorporated into the linear weight model with graph regularization. In one implementation, the objective function (3) can be redefined as follows:

$$\Omega_2(w) = \sum_i L(w^T x_i, y_i) + \alpha \cdot |w|_F^2 + \quad (4)$$

$$\beta \sum_{u_i,u_j \in N_u} \sum_{x \in A_{u_i}, y \in A_{u_j}} w_{u_i,u_j}((f(x) - f(y))^2,$$

where $N_u$ is a set of neighboring user pairs in the user preference graph (user pairs having the same preference), $A_{u_i}$ a set of all answers posted by user $u_i$, and $w_{u_i,u_j}$ is a weight of an edge between users and in the user preference graph. The term second summand can represent a graph regularization term to for minimizing an answer authenticity difference among users with a same preference. More particularly, this term can smooth labels on the user preference graph structure, where adjacent users with same preferences tend to post answers having a same label.

Figure 4:
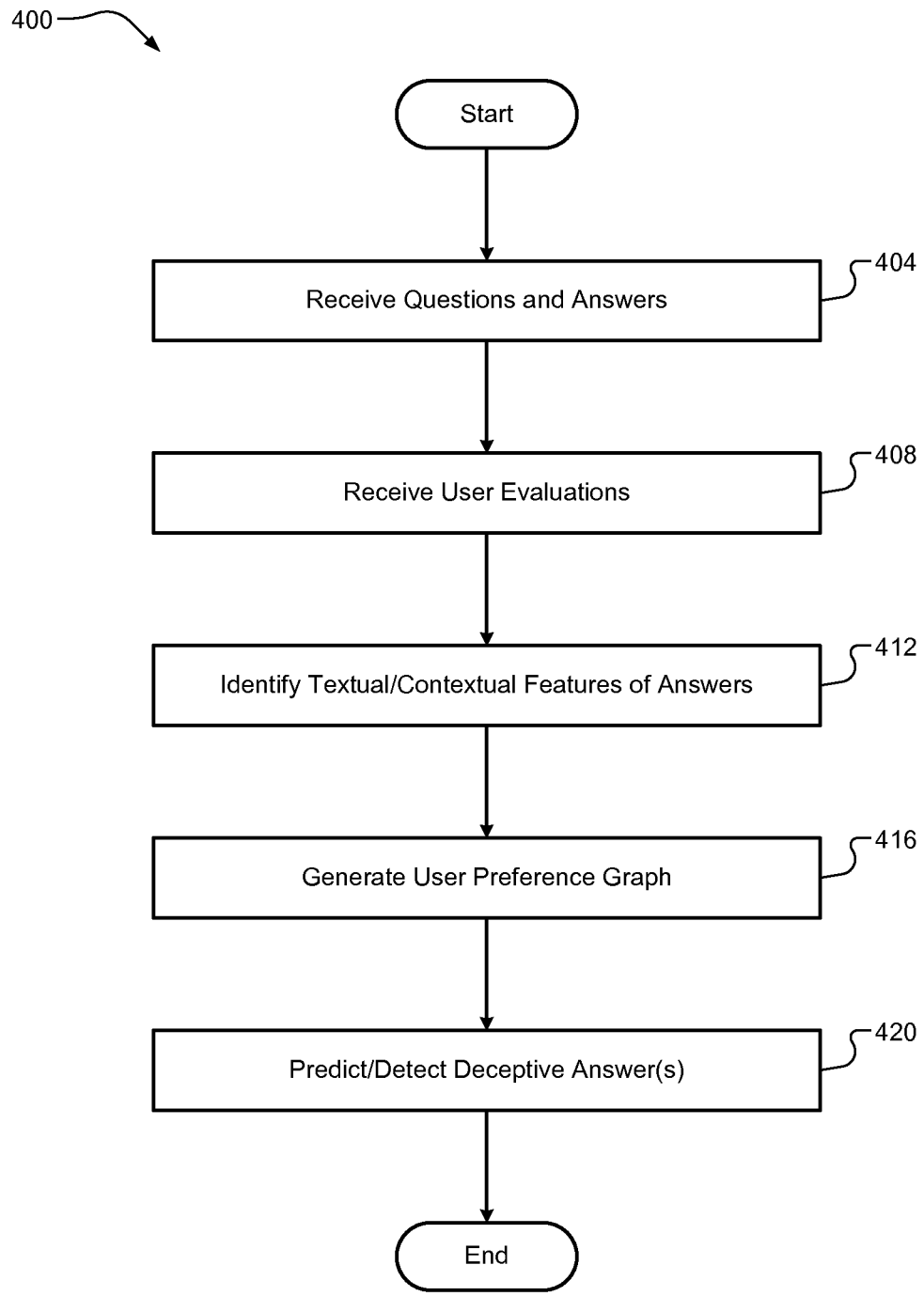
FIG. 4 is an example flow diagram of a technique for detecting deceptive answers to user questions based on user preference relationships according to some implementations of the present disclosure.

Referring now to FIG. 4, an example flow diagram of a method 400 for detecting deceptive answers based on user preference relationships is illustrated. At 404, the server 104 can receive questions and answers, each question having one or more answers, each question and each answer being associated with a particular user. For example, the questions and answers may be retrieved from a QA website hosted at the server 104 or another server. At 408, the server 104 can receive evaluations of the answers from users. At 412, the server 104 can identify at least one of textual and contextual features for each answer to obtain sets of features.

At 416, the server 104 can generate a user preference graph indicating relationships between users associated with at least one of the questions, the answers, and the evaluations. At 420, the server 104 can detect (or predict) whether a specific answer is a deceptive answer based on its set of features and the user preference graph. In general, a degree or a measure of deceptiveness for each answer can be determined, and in one example described herein, this degree or measure of deceptiveness can then be used to categorize an answer as deceptive or not deceptive, such as by comparing the degree or measure of deceptiveness for a specific answer to a threshold indicative of deceptive answers. The method 400 can then end.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known procedures, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The term "and/or" includes any and all combinations of one or more of the associated listed items. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

As used herein, the term module may refer to, be part of, or include: an Application Specific Integrated Circuit (ASIC); an electronic circuit; a combinational logic circuit; a field programmable gate array (FPGA); a processor or a distributed network of processors (shared, dedicated, or grouped) and storage in networked clusters or datacenters that executes code or a process; other suitable components that provide the described functionality; or a combination of some or all of the above, such as in a system-on-chip. The term module may also include memory (shared, dedicated, or grouped) that stores code executed by the one or more processors.

The term code, as used above, may include software, firmware, byte-code and/or microcode, and may refer to programs, routines, functions, classes, and/or objects. The term shared, as used above, means that some or all code from multiple modules may be executed using a single (shared) processor. In addition, some or all code from multiple modules may be stored by a single (shared) memory. The term group, as used above, means that some or all code from a single module may be executed using a group of processors. In addition, some or all code from a single module may be stored using a group of memories.

The techniques described herein may be implemented by one or more computer programs executed by one or more processors. The computer programs include processor-executable instructions that are stored on a non-transitory tangible computer readable medium. The computer programs may also include stored data. Non-limiting examples of the non-transitory tangible computer readable medium are nonvolatile memory, magnetic storage, and optical storage.

Some portions of the above description present the techniques described herein in terms of algorithms and symbolic representations of operations on information. These algorithmic descriptions and representations are the means used by those skilled in the data processing arts to most effectively convey the substance of their work to others skilled in the art. These operations, while described functionally or logically, are understood to be implemented by computer programs. Furthermore, it has also proven convenient at times to refer to these arrangements of operations as modules or by functional names, without loss of generality.

Unless specifically stated otherwise as apparent from the above discussion, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system memories or registers or other such information storage, transmission or display devices.

Certain aspects of the described techniques include process steps and instructions described herein in the form of an algorithm. It should be noted that the described process steps and instructions could be embodied in software, firmware or hardware, and when embodied in software, could be downloaded to reside on and be operated from different platforms used by real time network operating systems.

The present disclosure also relates to an apparatus for performing the operations herein. This apparatus may be specially constructed for the required purposes, or it may comprise a general-purpose computer selectively activated or reconfigured by a computer program stored on a computer readable medium that can be accessed by the computer. Such a computer program may be stored in a tangible computer readable storage medium, such as, but is not limited to, any type of disk including floppy disks, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each coupled to a computer system bus. Furthermore, the computers referred to in the specification may include a single processor or may be architectures employing multiple processor designs for increased computing capability.

The algorithms and operations presented herein are not inherently related to any particular computer or other apparatus. Various general-purpose systems may also be used with programs in accordance with the teachings herein, or it may prove convenient to construct more specialized apparatuses to perform the required method steps. The required structure for a variety of these systems will be apparent to those of skill in the art, along with equivalent variations. In addition, the present disclosure is not described with reference to any particular programming language. It is appreciated that a variety of programming languages may be used to implement the teachings of the present disclosure as described herein, and any references to specific languages are provided for disclosure of enablement and best mode of the present invention.

The present disclosure is well suited to a wide variety of computer network systems over numerous topologies. Within this field, the configuration and management of large networks comprise storage devices and computers that are communicatively coupled to dissimilar computers and storage devices over a network, such as the Internet.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A computer-implemented method, comprising:
   receiving, at a computing device having one or more processors, questions and answers, each question having one or more answers, and each question and each answer being associated with a particular user;
   receiving, at the computing device, evaluations of the answers from users;
   identifying, at the computing device, at least one of textual and contextual features for each answer to obtain sets of features;
   generating, at the computing device, a user preference graph indicating relationships between users associated with at least one of the questions, the answers, and the evaluations;
   determining, at the computing device, a measure of deceptiveness for each answer based on its set of features and the user preference graph; and
   detecting, at the computing device, whether each answer is a deceptive answer by comparing its measure of deceptiveness to a threshold indicative of deceptive answers.

2. The computer-implemented method of claim 1, further comprising determining, at the computing device, one or more additional features for each answer based on the user preference graph by regularizing the user preference graph and using a linear weight model.

3. The computer-implemented method of claim 2, wherein detecting whether each answer is deceptive includes detecting whether each specific answer is a deceptive answer based on its set of features and its one or more additional features.

4. The computer-implemented method of claim 1, wherein the evaluations indicate at least one of (i) a best answer for a specific question, (ii) an indication that a specific answer is helpful, and (iii) an indication that the specific answer is not helpful.

5. The computer-implemented method of claim 1, wherein the textual features for a specific question include at least one of:
   (i) a unigram;
   (ii) a bigram;
   (iii) a universal resource locator (URL);
   (iv) a phone number;
   (v) an electronic mail (e-mail) address; and
   (vi) a length of a specific answer; and
   wherein specific unigrams and bigrams corresponding to an intent to promote are indicative of deceptive answers, wherein URLs, phone numbers, and e-mail addresses are indicative of deceptive answers, and wherein lengthy answers are indicative of deceptive answers.

6. The computer-implemented method of claim 1, wherein the contextual features for a specific answer include a relevance to its corresponding question, and wherein a lack of relevance of the specific answer to its corresponding question is indicative of a deceptive answer.

7. The computer-implemented method of claim 6, further comprising determining, at the computing device, the relevance of a specific answer to its corresponding question by utilizing at least one of:
   (i) a vector space model;
   (ii) a translation model; and
   (iii) a topic model.

8. The computer-implemented method of claim 1, wherein the contextual features for a specific answer include at least one of:
   (i) past user activity statistics;
   (ii) a user authority score;
   (iii) robot-indicative features;
   (iv) evaluation from other users; and
   (v) duplication with other users.

9. The computer-implemented method of claim 1, wherein the questions, the answers, and the associated users are retrieved from a question/answer website.

10. The computer-implemented method of claim 1, further comprising:
    filtering, at the computing device, the answers to obtain filtered answers by removing the deceptive answers from the answers; and
    outputting, from the computing device, the filtered answers.

11. A computing device, comprising:
    a communication device configured to:
      receive questions and answers, each question having one or more answers, and each question and each answer being associated with a particular user; and
      receive evaluations of the answers from users; and
    one or more processors configured to:
      identify at least one of textual and contextual features for each answer to obtain sets of features;
      generate a user preference graph indicating relationships between users associated with at least one of the questions, the answers, and the evaluations;
      determine a measure of deceptiveness for each answer based on its set of features and the user preference graph; and
      detect whether each answer is a deceptive answer by comparing its measure of deceptiveness to a threshold indicative of deceptive answers.

12. The computing device of claim 11, wherein the one or more processors are further configured to determine one or more additional features for each answer based on the user preference graph by regularizing the user preference graph and using a linear weight model.

13. The computing device of claim 12, wherein the one or more processors are configured to detect whether each answer is a deceptive answer based on its set of features and its one or more additional features.

14. The computing device of claim 11, wherein the evaluations indicate at least one of (i) a best answer for a specific question, (ii) an indication that a specific answer is helpful, and (iii) an indication that the specific answer is not helpful.

15. The computing device of claim 11, wherein the textual features for a specific question include at least one of:
    (i) a unigram;
    (ii) a bigram;
    (iii) a universal resource locator (URL);
    (iv) a phone number;
    (v) an electronic mail (e-mail) address; and
    (vi) a length of a specific answer; and wherein specific unigrams and bigrams corresponding to an intent to promote are indicative of deceptive answers, wherein URLs, phone numbers, and e-mail addresses are indicative of deceptive answers, and wherein lengthy answers are indicative of deceptive answers.

16. The computing device of claim 11, wherein the contextual features for a specific answer include a relevance to its corresponding question, and wherein a lack of relevance of the specific answer to its corresponding question is indicative of a deceptive answer.

17. The computing device of claim 16, wherein the one or more processors are further configured to determine the relevance of each answer to its corresponding question by utilizing at least one of:
   (i) a vector space model;
   (ii) a translation model; and
   (iii) a topic model.

18. The computing device of claim 11, wherein the contextual features for a specific answer include at least one of:
   (i) past user activity statistics;
   (ii) a user authority score;
   (iii) robot-indicative features;
   (iv) evaluation from other users; and
   (v) duplication with other users.

19. The computing device of claim 11, wherein the questions, the answers, and the associated users are retrieved from a question/answer website.

20. The computing device of claim 11, wherein the one or more processors are further configured to filter the answers to obtain filtered answers by removing the deceptive answers from the answers, and wherein the communication device is further configured to output the filtered answers.

* * * * *